(12) United States Patent
Ni et al.

(10) Patent No.: US 12,098,379 B2
(45) Date of Patent: Sep. 24, 2024

(54) BARLEY MALE STERILITY GENE HvMSG47 AND USE THEREOF

(71) Applicant: SHANDONG AGRICULTURAL UNIVERSITY, Taian (CN)

(72) Inventors: Fei Ni, Taian (CN); Daolin Fu, Taian (CN); Juan Qi, Taian (CN); Jiajie Wu, Taian (CN)

(73) Assignee: SHANDONG AGRICULTURAL UNIVERSITY, Taian (CN)

( * ) Notice: Subject to any disclaimer, the term of this patent is extended or adjusted under 35 U.S.C. 154(b) by 0 days.

(21) Appl. No.: 17/723,806

(22) Filed: Apr. 19, 2022

(65) Prior Publication Data
US 2023/0332172 A1   Oct. 19, 2023

(51) Int. Cl.
C12N 15/82 (2006.01)
C07K 14/415 (2006.01)

(52) U.S. Cl.
CPC ........ *C12N 15/8289* (2013.01); *C07K 14/415* (2013.01)

(58) Field of Classification Search
None
See application file for complete search history.

(56) References Cited

FOREIGN PATENT DOCUMENTS

CN         101698850 A   *   4/2010

OTHER PUBLICATIONS

Pankin et al 2018 Targeted resequencing reveals genomic signatures of barley domestication, New Phytologist 218: 1247-1259 (Year: 2018).*
Zhang, X et al, 2022 The Plant Fatty Acyl Reductases, International Journal of Plant Sciences 23:16156 (Year: 2022).*
Guo et al, 2004, Protein tolerance to random amino acid change, Proceedings of the National Academy of Sciences, 101:9205-9210 (Year: 2004).*
Fernandez-Gomez and Wilson, 2014, A barley PHD finger transcription factor that confers male sterility by affecting tapetal developmentPlant Biotechnology Journal 12: 765-777 (Year: 2014).*
Chang et al, 2016, Construction of a male sterility system for hybrid rice breeding and seed production using a nuclear male sterility gene, Proceedings of the National Academy of Sciences, 113: 14145-14150 (Year: 2016).*
Zhou H et al, Development of Commercial Thermo-sensitive Genic Male Sterile Rice Accelerates Hybrid Rice Breeding Using the CRISPR/Cas9-neudated TMS5 Editing system, 2016, Scientific Reports 6:37395. (Year: 2016) (Year: 2016).*
Fan, Y and Zhang Q, Genetic and molecular characterization of photoperiod and thermo-sensitive male sterility in rice, 2018, Plant Reproduction 31: 33-14. (Year: 2018) (Year: 2018).*
Barman, NB et al, Generation of a new thermo-sensitive genic male sterile rice line by targeted mutagenesis of TMS5 gene through CRISPR/Cas9 system, 2019, BMC Plant Biology 19:109 (Year: 2019) (Year: 2019).*
Munoz-Amatriain, 2015, NCBI Accession: AC252157, https://www.ncbi.nlm.nih.gov/nuccore/AC252157 (Year: 2015).*
Aarts M et al, The *Arabidopsis* Male Sterility 2 protein shares similarity with reductases in elongation/condensation complexes. 1997, The Plant Journal 12(3): 615-623 (Year: 1997).*
Uniprot A0A3B6IWP9 2022 (Year: 2022).*
Druka et al 2011, Plant Physiology 155: 617-627 and Supplemental Table 1 (Year: 2011).*
Franckowiak et al 2015, Barley Genetics Newsletter 45 1-251; wheat.pw.usda.gov/ggpages/bgn/45/Barley_Genetics_Newsletter_v45.pdf (Year: 2015).*
NCBI Accession AK373931, 2011, ncbi.nlm.nih.gov/nucleotide/AK373931.1 (Year: 2011).*
Guo-hui Ma et al.; "Hybrid rice achievements, development and prospect in China"; Journal of Integrative Agriculture; 2015; vol. 14; No. 2; pp. 197-205.
Letian Chen et al.; "Male Sterility and Fertility Restoration in Crops"; Annual Review of Plant Biology; 2014; vol. 65; pp. 579-606 and Contents.
Zhengyi Chang et al.; "Construction of a male sterility system for hybrid rice breeding and seed production using a nuclear male sterility gene"; PNAS; 2016; vol. 113; No. 49; pp. 14145-14150.
Zheng Wang et al.; "Poaceae-specific MS1 encodes a phospholipid-binding protein for male fertility in bread wheat"; PNAS; 2017; vol. 114; No. 47; pp. 12614-12619.
Stephen F. Altschul et al.; "Basic Local Alignment Search Tool"; J. Mol. Biol.; 1990; vol. 215. pp. 403-410.
Samuel Karlin et al.; "Applications and statistics for multiple high-scoring segments in molecular sequences"; Proc. Natl. Acad. Sci. USA; 1993; vol. 90; pp. 5873-5877.
Kai Wang et al.; "ANNOVAR: functional annotation of genetic variants from high-throughput sequencing data"; Nucleic Acids Research; 2010; vol. 38; No. 16; pp. 1-7.

* cited by examiner

Primary Examiner — Anne Kubelik
Assistant Examiner — Aleksandar Radosavljevic
(74) Attorney, Agent, or Firm — Oliff PLC (57) ABSTRACT

A barley male sterility gene HvMSG47, wherein the gene HvMSG47 is (i) a nucleotide sequence as set forth in SEQ ID NO: 1. (ii) a nucleotide sequence as set forth in SEQ ID NO: 2, or (iii) a nucleotide sequence that has 90% or more homology with the nucleotide sequence of (i) or (ii) and expresses the same functional protein.

9 Claims, 2 Drawing Sheets
Specification includes a Sequence Listing.

BARLEY MALE STERILITY GENE HvMSG47 AND USE THEREOF

SEQUENCE LISTING

The present application contains a Sequence Listing that has been submitted electronically in ASCII format and is hereby incorporated by reference in its entirety. The ASCII copy, created on May 16, 2024, is named Substitute_Sequence_Listing_ST25.txt and is 21,880 bytes in size.

TECHNICAL FIELD

The present invention relates to the technical field of plant genetic engineering and specifically relates to a barley male sterility gene HvMSG47 and use thereof.

BACKGROUND TECHNOLOGY

Barley is the fourth largest food crop in China, which is mainly used as feed, grain and beer raw materials and plays an important role in the national economy. With the continuous increase of population and the improvement of living standard, China's food demand is showing a rigid growth. Grain yield is closely related to the production and application of crop hybrids. Among the four major food crops, corn hybrids play an important role in the super-high yield process, making its yield leap to the first place in China since 2012 (China Statistical Yearbook, 2017). For rice, the wide application of hybrid rice has promoted the increase of rice yield by more than 20% in China, and its planting area has reached more than 50% of the total rice planting area (Yuan, 2015). However, for the utilization of wheat and barley hybrids, although some breakthroughs have been made in recent years, such as the improvement of the purity of wheat hybrid seed production and the identification of male sterile germplasm resources, wheat crops hybrids have not been produced and utilized on a large scale. Wheat and barley are strictly self-pollinated crops, the maintenance and recovery of male sterility traits is the key to hybrid production, the discovery and identification of good male sterility genes is the premise of hybrid production. In addition, barley is diploid, its genome is relatively simple and has close relationship with wheat, so it is a good model material for genetic research of wheat crops. Therefore, it is important to isolate the male sterility gene of barley by forward genetics for hybrid seed production of barley and wheat.

Plant male sterility refers to the phenomenon that stamens develop abnormally and cannot produce normal anthers, pollen or male gametes, but pistils develop normally and can accept foreign pollen and fertilize and seed. Plant male sterility mainly includes cytoplasmic male sterility (CMS) and genic male sterility (GMS). Plant male sterility provides important materials for studying pollen development, cytoplasmic genetics and nucleo-cytoplasmic interactions, and also becomes an important tool for carrying out heterosis, recurrent selection and population improvement of crops. Plant male sterility is an important tool to develop heterosis and is widely used in crop hybrid breeding. The related hybrid seed production techniques can be divided into "three-line system" and "two-line system" (Chen et al., 2014). The CMS-based hybrid seed production technique is called "three-line system", i. e., three breeding lines are required: CMS sterile line, sterile maintainer line and sterile restorer line. In contrast to CMS, most GMS have not been used for hybrid seed production, and the main difficulty is that maintenance and recovery of the GMS sterility gene cannot be effectively achieved. Environmental sensitive GMS overcomes this shortcoming and plays an important role in crop hybrid seed production, which is called "two-line system". The environmental sensitive GMS line is used as a male sterile line under restrictive conditions (long-day or high-temperature conditions) and fertile under normal conditions (short-day or low-temperature conditions) and can be used as a maintainer line for reproduction; other lines carrying normally fertile genes can be used as male parents to pollinate environmentally sensitive GMS lines under restrictive conditions to obtain fertility-restored $F_1$ hybrids. In recent years, the third generation hybrid technology based on recessive male sterility gene and genetic engineering has been gradually matured in rice and wheat (Chang et al., 2016; Wang et al., 2017). The premise of this technology is to obtain male sterility gene with complete abortion. The advantage of this technology is to obtain 100% sterile recessive nuclear sterile population, and to obtain hybrid $F_1$ without transgenic components. The hybrid $F_1$ is a new type of sterile hybrid breeding system with stability and high efficiency and the integration of male sterile line and maintainer line. Whether it is the "three-line system", "two-line system", or the third-generation hybridization technology based on genetic engineering, the discovery and identification of thoroughly abortive male sterility gene is the premise of plant heterosis utilization.

CONTENT OF INVENTION

With regard to the above-mentioned prior art, after long-term research and exploration of the present invention, the barley male sterility mutant material GSHO 2400 (the male sterility phenotype of which is controlled by the HvMSG47 gene) is selected as a female parent and the barley cultivar Morex as a male parent to construct a mapping population of map-based cloning, wherein the HvMSG47 is located in a genetic interval of 1.55 cM, corresponding to about 2.14 Mb in the physical map, comprising 32 candidate genes; finally, the barley male sterility gene HvMSG47 is identified by expression pattern analysis and haplotype analysis of annotated genes. Mutations in this gene can lead to the phenotype of male sterility in barley, which can produce new male sterile materials and have important application value in scientific research and agricultural production.

In the first aspect of the present invention, a barley male sterility gene HvMSG47 is provided, where the gene HvMSG47 is:
  i) a nucleotide sequence as set forth in SEQ ID NO: 1; or
  ii) a nucleotide sequence as set forth in SEQ ID NO: 2; or
  iii) a nucleotide sequence that has 90% or more homology with the nucleotide sequence of i) or ii) and expresses the same functional protein.

In the second aspect of the present invention, a use of the gene HvMSG47 in the regulation of pollen development in plants is provided, wherein the gene HvMSG47 is selected from the group consisting of:
  a) a DNA fragment as set forth in SEQ ID NO: 1;
  b) a DNA fragment as set forth in SEQ ID NO: 2;
  c) a DNA fragment other than b) encoding the amino acid sequence as set forth in SEQ ID NO: 3;
  d) a DNA fragment, which has 90% or more than 90% identity with the DNA fragment defined in a) or b), and the encoded protein is functionally equivalent to the protein as set forth in SEQ ID NO: 3.

As a barley male sterility gene, HvMSG47 gene mutation will result in no pollen grains in anthers of barley stamens, resulting in male sterility, self-sterility, but normal pistil development. Thus, the gene HvMSG47 can regulate pollen development in plants.

In the third aspect of the present invention, a use of recombinant expression vectors, transgenic cell lines or genetically engineered bacteria carrying the gene HvMSG47 as described above for regulating pollen development in plants is provided.

In the fourth aspect of the present invention, a use of a protein for regulating pollen development in plants is provided, wherein the protein is selected from the group consisting of:
1) an amino acid sequence of the protein as set forth in SEQ ID NO: 3;
2) a protein having the same function as the protein as set forth in SEQ ID NO: 3 obtained by replacing, deleting or inserting the amino acid sequence as set forth in SEQ ID NO: 3 with one, several or several tens of amino acids;
3) a fusion protein obtained by attaching a tag to a N-terminus and/or a C-terminus of the protein as set forth in SEQ ID NO: 3.

In the fifth aspect of the present invention, a use of the gene HvMSG47 in creating a plant male sterile line is provided; where the gene HvMSG47 is selected from the group consisting of:
a) a DNA fragment as set forth in SEQ ID NO: 1;
b) a DNA fragment as set forth in SEQ ID NO: 2;
c) a DNA fragment other than b) encoding the amino acid sequence as set forth in SEQ ID NO: 3;
d) a DNA fragment, which has 90% or more than 90% identity with the DNA fragment defined in a) or b), and the encoded protein is functionally equivalent to the protein as set forth in SEQ ID NO: 3.

In the sixth aspect of the present invention, a use of the gene HvMSG47 in hybrid breeding or seed production of plants is provided; where the gene HvMSG47 is selected from the group consisting of:
a) a DNA fragment as set forth in SEQ ID NO: 1;
b) a DNA fragment as set forth in SEQ ID NO: 2;
c) a DNA fragment other than b) encoding the amino acid sequence as set forth in SEQ ID NO: 3;
d) a DNA fragment, which has 90% or more than 90% identity with the DNA fragment defined in a) or b), and the encoded protein is functionally equivalent to the protein as set forth in SEQ ID NO: 3.

In the seventh aspect of the present invention, a method of creating a plant male sterile line is provided, wherein the method comprises the step of causing reduced or no expression of a polynucleotide contained in plants, wherein the polynucleotide is selected from the group consisting of:
a) a DNA fragment as set forth in SEQ ID NO: 1;
b) a DNA fragment as set forth in SEQ ID NO: 2;
c) a DNA fragment other than b) encoding the amino acid sequence as set forth in SEQ ID NO: 3;
d) a DNA fragment, which has 90% or more than 90% identity with the DNA fragment defined in a) or b), and the encoded protein is functionally equivalent to the protein as set forth in SEQ ID NO: 3.

Or the method consists of the step of reducing or losing the activity of the protein in the plants containing the protein selected from the group consisting of:
1) an amino acid sequence of the protein is as set forth in SEQ ID NO: 3;
2) a protein having the same function as the protein as set forth in SEQ ID NO: 3 obtained by replacing, deleting or inserting the amino acid sequence as set forth in SEQ ID NO: 3 with one, several or several tens of amino acids.

Preferably, the method of reduced expression or no expression of the polynucleotide consists of: mutating or knocking out all or part of the sequence of the polynucleotide; or constructing an interference vector to interfere with expression of the polynucleotide; alternatively, expression of the polynucleotide is silenced using a gene silencing system.

As a preferred embodiment, the present invention provides a method of creating a plant male sterility line comprising the steps of:
deleting amino acids located at positions 530 to 540 of the protein as set forth in SEQ ID NO: 3 in plants.

In the eighth aspect of the present invention, a method of restoring pollen fertility of a male sterile line of a plant is provided, the method comprises the steps of: transferring an exogenous gene HvMSG47 into the male sterile line of plants, so as to restore the wild-type phenotype of the mutant. The exogenous gene HvMSG47 is selected from the group consisting of:
a) a DNA fragment as set forth in SEQ ID NO: 1;
b) a DNA fragment as set forth in SEQ ID NO: 2;
c) a DNA fragment other than b) encoding the amino acid sequence as set forth in SEQ ID NO: 3;
d) a DNA fragment, which has 90% or more than 90% identity with the DNA fragment defined in a) or b), and the encoded protein is functionally equivalent to the protein as set forth in SEQ ID NO: 3.

In the above-mentioned use or method, the "plant" or "plants" mentioned may be all species which exhibit male sterility after utilization of the gene HvMSG47. The plants comprise: plants carrying the gene HvMSG47; and/or plants in which the gene HvMSG47 or a mutant of the gene HvMSG47 has been transferred exogenously.

Preferably, the plants specifically include, but is not limited to: barley, wheat, rice, brachypodium and the like.

The beneficial effects of the present invention:

The present invention isolates a complete DNA fragment of male sterility related gene HvMSG47 from the barley male sterility mutant material GSHO 2400 for the first time, and verifies its function through mutant screening technology. It is proved that the mutation of HvMSG47 gene can lead to the male sterility phenotype of barley. Therefore, the barley male sterility gene HvMSG47 discovered in the present invention will play an important role in plant heterosis utilization and hybrid seed production.

SPECIFIC EMBODIMENTS

Noted that the following detailed description is exemplary and is intended to provide further explanation for the application. Unless otherwise specified, all technical and scientific terms used herein have the same meanings as commonly understood by those of ordinary skill in the technical field to which this application belongs.

As described in the background technology, the discovery and identification of thoroughly abortive male sterility gene is the premise of crop heterosis utilization. Barley has abundant GMS gene resources, but because there is no ideal maintainer, GMS gene has not been widely used in barley hybrid seed production. At present, only msg6 is widely used in recurrent selection of conventional barley breeding. The total yield of barley in China is low and depends on import seriously. Therefore, improving barley yield is an important breeding target in China, and it is urgent to develop new male sterility genes in barley.

In order to develop a new barley male sterility gene, the present invention uses the barley male sterility mutant material GSHO 2400 and the barley cultivar Morex to construct a mapping population; barley male sterility mutant material GSHO 2400 is a naturally occurring mutant material from Barley Genetic Stocks Database (www.nordgen.org/bgs), barley male sterility mutant material GSHO 2400 is a type of male sterile without pollen grains, self-sterility, but normal pistil development, can accept foreign pollen to restore fertility, its male sterility phenotype is controlled by recessive single gene HvMSG47. In the present invention, BSR-Seq combined with chromosome walking technology is used to isolate HvMSG47 gene, and functional verification is performed through mutant screening and sequencing, which proved that HvMSG47 gene mutation can cause male sterility phenotype in barley.

The HvMSG47 gene is located on the 4HL chromosome of barley, and the full-length gDNA sequence of the gene is as set forth in SED ID NO. 1; the full-length cDNA sequence of the gene is as set forth in SEQ ID NO: 2; the amino acid sequence of the encoded protein is as set forth in SED ID NO. 3.

Based on the discovery of the barley male sterility gene HvMSG47 described above, the scope of the present invention also includes DNA fragments homologous to the above genes, as long as the protein they encode is functionally equivalent to the protein as set forth in SEQ ID NO: 3. As referred to herein, "functionally equivalent to the protein as set forth in SEQ ID NO: 3" means that the protein encoded by the target DNA fragment is the same or similar to the protein as set forth in SEQ ID NO: 3 of the present invention in terms of biological function, physiological and biochemical characteristics and the like. The typical biological function of the proteins shown by SEQ ID NO: 3 is to regulate pollen development in plants. Down regulation of the expression and/or activity of the protein as set forth in SEQ ID NO: 3 can result in abnormal stamen development in plants, and no pollen grains in the anther of stamens.

These DNA fragments homologous to the gene HvMSG47 include alleles, homologous genes, mutant genes and derivative genes corresponding to the nucleotide sequences of the present invention (SEQ ID NO: 1 and SEQ ID NO: 2); the proteins they encode are similar to the proteins as set forth in SEQ ID NO: 3 of the present invention, or the presence of one, several or tens of amino acid substitutions, deletions or insertions are within the scope of the present invention.

Those of ordinary skill in the art can readily mutate the nucleotide sequence of the non-critical sites of the HvMSG47 gene of the present invention using known methods, such as directed evolution and point mutation. Those nucleotides that have been artificially modified to have 90% or more identity to the nucleotide sequence of the HvMSG47 gene of the present invention, such as 90%, 92%, 94%, 96%, 97%, 98% or 99%, are derived from and identical to the nucleotide sequence of the present invention as long as the encoded protein is functionally equivalent to the protein as set forth in SEQ ID NO: 3.

As used herein, the term "identity" refers to sequence similarity to natural nucleic acid sequences. "Identity" includes nucleotide sequences that are 90% or more, or 95% or more, or 99% or more identical to the nucleotide sequence as set forth in SEQ ID NO: 1 of the present invention. Equivalence rates of amino acid or nucleotide sequences can be determined using the BLAST algorithm (Altschul et al. 1990. Journal of Molecular Biology 215:403-410; Karlin and Altschul. 1993. Proceedings of the National Academy of Sciences 90:5873-5877).

However, mutations at a key site in the HvMSG47 gene can lead to a male sterility phenotype in barley, and analysis of the cDNA sequence of HvMSG47 (SEQ ID NO: 2) according to the present invention indicates that it is a barley gene encoding a Fatty acyl-CoA reductase. The protein encoded by HvMSG47 (SEQ ID NO: 3) is predicted to have two conserved domains at the Pfam 32.0 website (pfam.xfam.org), NAD-binding 4 domain and Sterile domain. The naturally occurring mutant GSHO 2400 according to the present invention has a 33 bp sequence deletion in the coding region of the HvMSG47 gene, resulting in a change in the amino acid sequence of Fatty acyl-CoA reductase in GSHO 2400, that is, an 11-amino acid deletion of SIYQPY-TFYTG (SEQ ID NO: 28), which deletion is located in sterile domain and finally results in GSHO 2400 exhibiting a male sterility phenotype. In the present invention, three male sterility mutants (respectively named as N6807, N6405 and N 11133) are screened from the barley mutant library, all of which had SNP in the coding region of HvMSG47, where the SNP in N6807 is located in the first exon, resulting in an amino acid change, denoted as G75D; SNP in N6405 is located in the 3rd exon, resulting in an amino acid change, denoted as A202V and located in NAD-binding 4 domain; SNP in N11133 is located in 9th exon, resulting in an amino acid change, denoted V566E and located in Sterile domain. The mutant variants G74D, A202V, and V566E are set forth in SEQ ID NO: 29. Although the G74D mutation in N6807 did not occur in NAD-binding 4 domain and sterile domain, this mutant also showed the phenotype of male sterility, so it is speculated that the N-terminal of HvMSG47 gene might contain signal peptide, and the G74D mutation might result in the change of signal peptide activity, thus leading to the phenotype of male sterility.

In order to enable those skilled in the art to understand the technical scheme of this application more clearly, the technical scheme of this application will be described in detail with specific embodiments below.

The test materials used in the embodiments and comparative examples of the present invention are all conventional test materials in the field and can be purchased through commercial channels. Test methods without detailed conditions are carried out according to conventional test methods or operating instructions recommended by suppliers.

Figure 1:
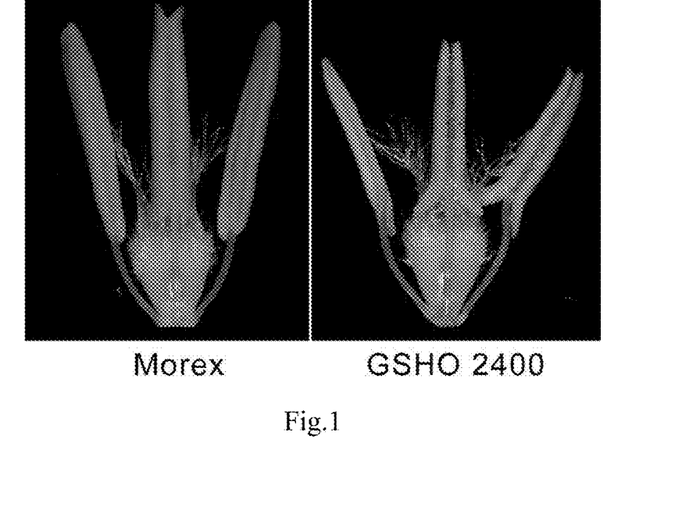
FIG. 1: anther of wild type barley Morex and male sterile mutant GSHO 2400.
Figure 2:
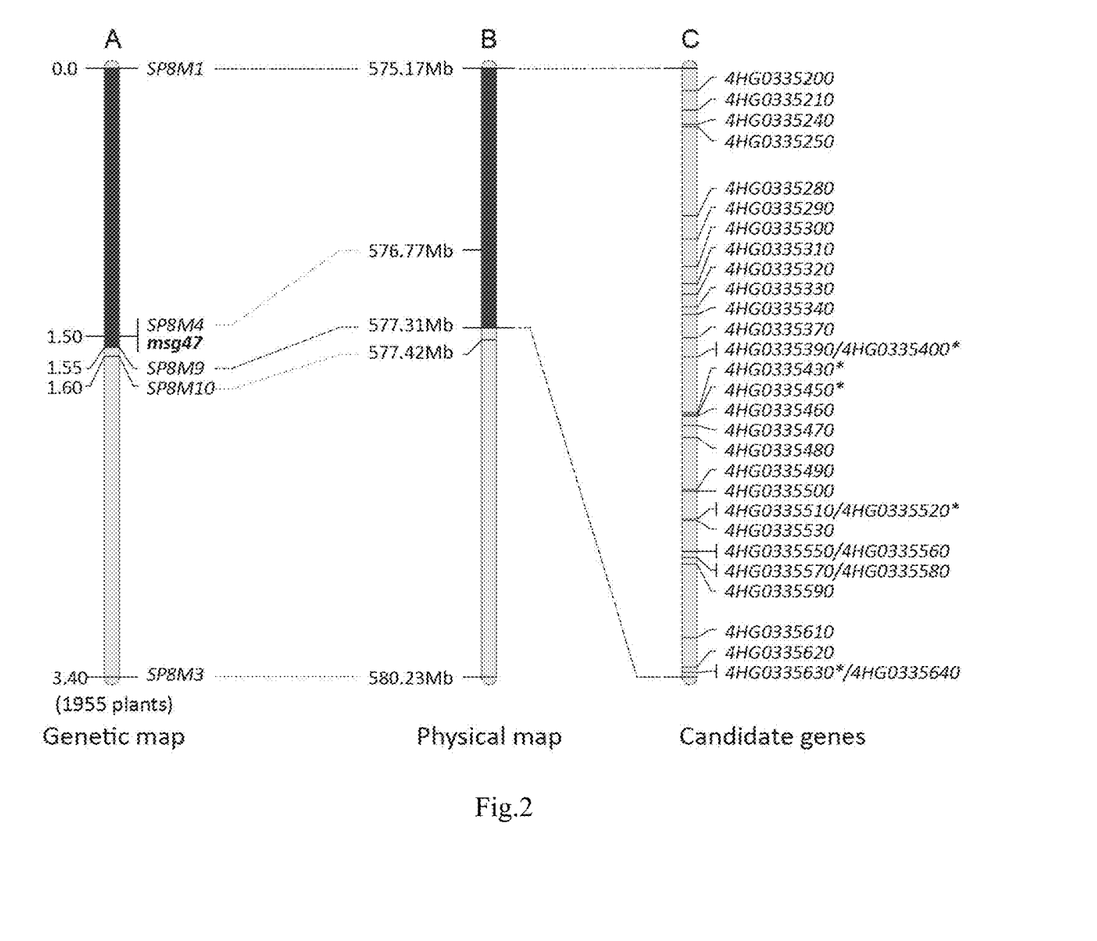
FIG. 2: the present invention maps the genetic map (A), the physical map (B) and the annotated gene (C) of the HvMSG47 gene. (A) Black region of genetic map is the linkage region; the unit of genetic map is centimorgan (cM), which is marked on the left side of the map, molecular markers are marked on the right side of the map, size and name of $F_2$ population are marked below the map, and size of $F_2$ population in parentheses; (B) the HvMSG47 gene maps to barley 4HL: 575.17 Mb to 577.31 Mb; (C) the candidate interval contains 32 annotated genes, and 5 anther-specific expressed genes are marked with *.

Embodiment 1: Isolation and Cloning of HvMSG47 Gene and Identification of Candidate Genes 1. Genetic Mapping of the HvMSG47 Gene:

The male sterility phenotype of the barley material GSHO 2400 is as set forth in FIG. 1. The present invention uses BSR-Seq technology in combination with forward genetics to isolate the barley male sterility gene HvMSG47. In the present invention, an $F_2$ mapping population is constructed using barley cultivar Morex as a male parent and barley male sterility mutant material GSHO 2400. The construction of HvMSG47 genetic map includes two parts: preliminary mapping and fine mapping: the population used for preliminary mapping is an $F_2$ population (PopM47-1) containing 262 individual plants. The polymorphic sites used for molecular markers are derived from BSR-Seq and transformed into two CAPS markers (SP8M1 and SP8M3). HvMSG47 is located in the genetic interval of about 3.4 cM on 4HL. In fine mapping, the $F_2$ population is expanded to 1,995 individual plants (including the initial mapping population PopM47-1), and 3 molecular markers are newly developed. Finally, HvMSG47 is mapped to an interval of about 1.55 CM (FIG. 2A), corresponding to a physical interval of about 2.14 Mb (FIG. 2B), corresponding to 32 annotated genes (FIG. 2C).

The PCR labels used in this embodiment are detailed in Table 1. Forward and reverse primers for amplification of each molecular marker are as set forth in SEQ ID NO: 4 to SEQ ID NO: 13, respectively.

TABLE 1

Used PCR labels

| Label | Forward and reverse primers (5' to 3') | Annealing temperature (° C.) | Endonuclease | PCR product size (bp)[a] |
|---|---|---|---|---|
| SP8M1 | CTTCAATACATTTC CAGACCGGC ACTTACAATACCTT GCTGAATGGGC | 60 | TaqI | M (293 + 178); G (471) |
| SP8M3 | CTCATTTCGAGCTG AGAGAGAGC CCTATCGGGCATTT GTTCACCG | 60 | HinfI | M (464); G (227 + 237) |
| SP8M4 | CTCTTCGACACCAT GGAGCAG CAAAACATATGCGT CGACAAACGG | 61 | — | M (250); G (217) |
| SP8M9 | AAAAGTCATACTGC CACGGTCCG AGTAGGGAAATCTT GCTCCCCTC | 61 | BccI | M (188); G (130 + 58) |
| SP8M10 | TTCCCCTCCTTCCTG TATCGGCCCG ATCCCCGTGCGGGC GCTTTGA | 66 | SmaI | M (242); G (220 + 22) |

Note:
[a]male fertile material Morex (M), male abortive material GSHO 2400 (G).

Figure 3:
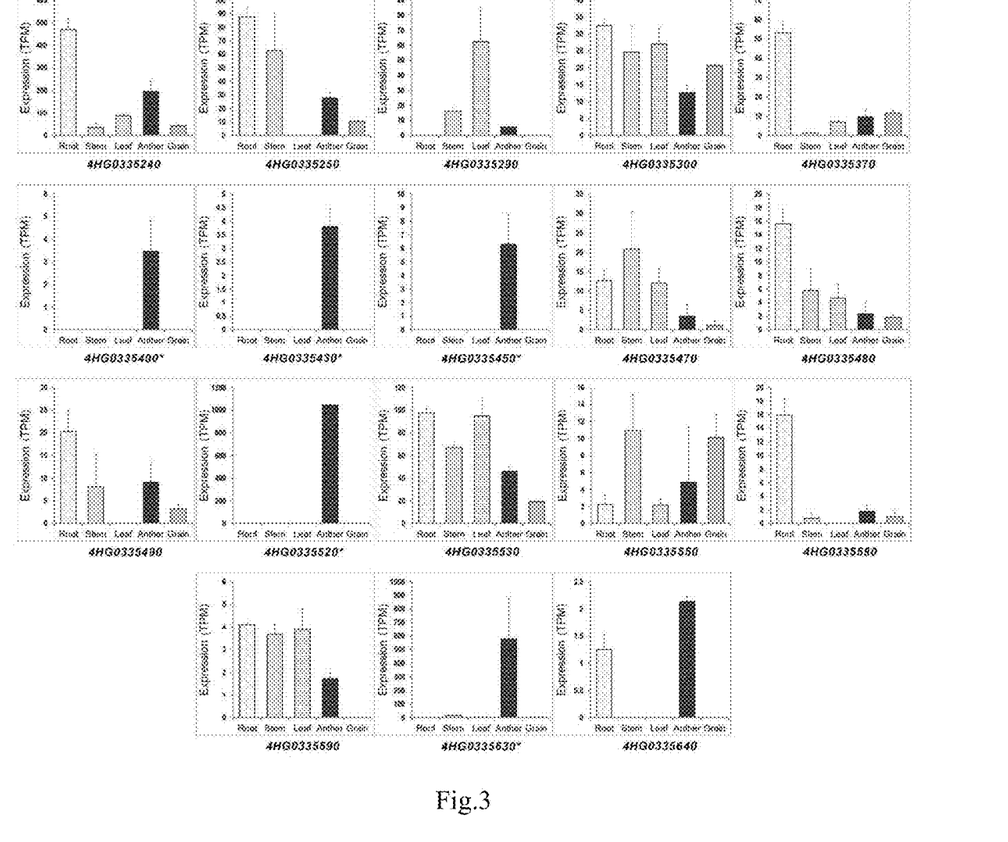
FIG. 3: expression patterns of candidate genes. Among them, 4HG0335400, 4HG0335430, 4HG0335450, 4HG0335520 and 4HG0335630 show anther-specific expression patterns.

2. Identification of HvMSG47 Candidate Genes:

In order to screen candidate genes according to the present invention, anthers of fertile materials before and after meiosis are selected for RNA-Seq sequencing and quantitative analysis of gene expression. Leaf ring distance and young panicle length can be used as indicators to predict anther development stage. Carbol fuchsin staining of barley anthers and pollen shows that when the leaf ring distance is between −6 cm to −3 cm and the panicle length is between 2 cm to 5 cm, most of the anthers in young panicles are in meiosis. According to the present invention, anthers are sampled according to this standard, and equal amounts of anthers at three developmental stages of meiosis period and before and after meiosis are respectively selected and mixed for RNA sequencing. At the same time, in order to ensure the consistency of samples, anthers are collected only from 3 to 5 florets in the middle of young spike, the obtained samples are immediately placed in liquid nitrogen for preservation, 3 biological replicates are taken, and RNA extraction, quality inspection and subsequent library construction sequencing are similar to BSR-Seq. Combining the expression data of root, stem, leaf and grain, leaf and grain in the common RNA-Seq data (NCBI BioProject PRJEB14349) of barley and the expression data of anther measured in the present invention, the inventors perform quantitative analysis of gene expression in different tissues using salmonv0.14.1 (combine-lab.github.io/salmon). The results show (FIG. 3) that 18 expressed genes could be detected in anthers, of which 5 genes exhibit the characteristics of anther-specific expression. These 5 genes are: 4HG0335400, 4HG0335430, 4HG0335450, 4HG0335520 and 4HG0335630 (marked with * in FIG. 2C and FIG. 3).

The present invention uses DNA resequencing technology to perform polymorphism analysis on the abortive parent GSHO 2400 and the fertile parent Morex to further screen candidate genes. The specific methods are as follows: the flag leaf DNA of the two parents are extracted by the conventional CTAB method and resequenced by DNA resequencing technology. Illumina Novaseq is used as the sequencing platform. The size of the library is about 300 bp, the length of the sequencing read is PE 150 bp, the sequence data is 100 Gb/sample, and the sequencing depth is about 20×. Using gramineous repetitive sequence database mipsREdat 9.3p (pgsb.helmholtz-muenchen.de) as the reference sequence to filter the clean data obtained by sequencing, and only the non-repetitive sequence is reserved for routine polymorphism detection to improve the efficiency of data analysis. BWA (bio-bwa.sourceforge.net) is used to complete the data comparison, samtools v1.5 (www.htslib.org) is used to extract the comparison results of the target interval (2.14 Mb), and GATK v3.8 (gatk.broadinstitute.org) is used to detect the polymorphism of the target interval. Functional annotation of polymorphic sites is done using ANNOVAR (Wang et al. 2010, Nucleic Acids Research, 38:e164).

The resequencing results and functional annotation show that compared with the fertile parent Morex, the above-mentioned five anther-specific expression genes have three SNPs (T324C, T344G and A420C) in the coding region of the gene 4HG0335400 in the abortive material GSHO 2400, but none of them causes amino acid changes. A 33 bp deletion in the coding region of gene 4HG0335520 results in a deletion of 11 amino acids (SIYQPYTFYTG-SEQ ID NO: 28) in the conserved domain of the corresponding protein. The remaining three genes, 4HG0335430, 4HG0335450 and 4HG0335630, have no polymorphic at the cDNA level. Thus, the present invention uses 4HG0335520 as a candidate gene for HvMSG47 for subsequent mutant validation.

Embodiment 2: Functional Verification of HvMSG47 Gene

In order to verify whether the HvMSG47 gene is related to plant male sterility, the present invention carried out haplotype analysis on over 100 male sterile lines of barley collected or created in the laboratory. According to the present invention, the flag leaf DNA of the above-mentioned male sterile genetic material are respectively extracted by the conventional CTAB method, and the gene 4HG0335520 is amplified and sequenced using specific primers. The relevant primers are as follows:

```
4HG0335520-F1:
                                (SEQ ID NO: 14)
5'-TGT TCA GAG GGA GTA AAC TAT CGA-3';

4HG0335520-R1:
                                (SEQ ID NO: 15)
5'-CAT GGA TGT CAT GCG ACA CAA C-3';

4HG0335520-F2:
                                (SEQ ID NO: 16)
5'-TAC CAC CTA GAT TCA GTC ACT CC-3';

4HG0335520-R2:
                                (SEQ ID NO: 17)
5'-GAA CAA ACC TGG TAC AAT GAC ATC-3';
```

Figure 4:
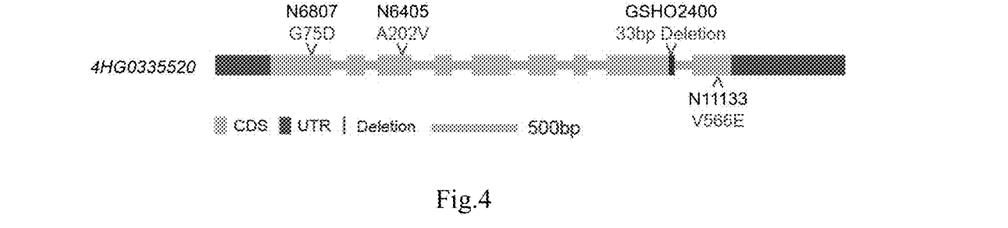
FIG. 4: haplotype analysis of candidate genes.

Sequencing results showed that three male sterile lines (named N6807, N6405 and N11133), all had one SNP in the coding region of 4HG0335520 gene, and these SNPs all caused amino acid changes (FIG. 4). The SNP in N6807 is located in the first exon, and the mutation is G74D at amino acid level. SNP in N6405 is located in the third exon, and the mutation at amino acid level is A202V, which is located in NAD-binding 4 domain; the SNP in N11133 is located in the 9th exon, the mutation at amino acid level is V566E, which is located in sterile domain. Although the G74D mutation in N6807 did not occur in NAD-binding 4 domain and sterile domain, the mutant also showed a phenotype of male sterility, therefore, it is speculated that the N-terminal of 4HG0335520 gene may contain a signal peptide, while the G74D mutation may result in the change of signal peptide activity, thus leading to the phenotype of male sterility.

In summary, the present invention proves that the 4HG0335520 gene is the barley male sterility gene HvMSG47 through four independent mutants (including: GSHO2400, N6807, N6405 and N11133).

Embodiment 3: Gene Editing Test in Wheat

1. Test Methods 1.1 CRISPR/Cas 9 Target Design:

The CDS sequence of the homologous genes (TraesCS4A01G020500, TraesCS4B01G283200, TraesCS4D01G282000) of barley HvMsg47 in wheat is imported into the E-crispr website(www.e-crisp.org/E-CRISP/designcrispr.html) to design gRNA target, and the specificity of the target is detected by Ensemble plant website(plants.ensembl.org/index.html).

1.2 Target Site

Two sgRNA are designed according to the first exon and the third exon of MSG47-4A (TraesCS4A01G020500), MSG47-4B (TraesCS4B01G283200), MSG47-4D (TraesCS4D01G282000), respectively, and the sgRNA are constructed on the CRISPR/Cas9(pBUE413) vector. The target sequences information of CRISP/Cas9 are as follows:

```
Target1:
                                (SEQ ID NO: 18)
CCTTGCCGGTGCACGGCAAGAGC;

Target2:
                                (SEQ ID NO: 19)
CCACCTTCGACGAGAGGTTCGTC;
```

1.3 Primer Design

```
P121:
                                (SEQ ID NO: 20)
AAGCACGGTCAACTTCCGTA;

P122:
                                (SEQ ID NO: 21)
GAAGTCCAGCTGCCAGAAAC;

MSG47-CRISP-WheatA-SF1:
                                (SEQ ID NO: 22)
CCGATCAGCTCCACCATCAC;

MSG47-CRISP-WheatA-SR1:
                                (SEQ ID NO: 23)
ATCTTGGAGCAGTGCAAACAGC;

MSG47-CRISP-WheatB-SF2:
                                (SEQ ID NO: 24)
CTAGCCCGTACCTGACGAC;

MSG47-CRISP-WheatB-SR2:
                                (SEQ ID NO: 25)
ATGGCATGAGCCTGACCTGTG;

MSG47-CRISP-WheatD-SF3:
                                (SEQ ID NO: 26)
CTTTCCGTGTTCTTCCCACAC;

MSG47-CRISP-WheatD-SR3:
                                (SEQ ID NO: 27)
AGACCGAGACCAAGAGGAGG;
```

P121/122 is BAR gene detection primer, MSG47-CRISP-WheatA-SF1/SR1, MSG47-CRISP-WheatB-SF2/SR2, MSG47-CRISP-WheatD-SF3/SR3 are three subgenomic specific primers of A, B, and D, corresponding to TraesCS4A01G020500, TraesCS4B01G283200 and TraesCS4D01G282000, respectively.

1.4 Detection Methods 1.4.1 BAR Gene PCR Amplification

BAR gene PCR amplification uses Vazyme Green Taq Mix kit, and the specific reaction system is as follows:

| | |
|---|---|
| Total volume | 15 μl |
| Mix | 7.5 μl |
| DNA | 1 μl |
| Forward Primer | 0.5 μl |
| Reverse Primer | 0.5 μl |
| ddH$_2$0 | 5.5 μl |

The reaction conditions: annealing temperature 57° C., with extension time 25 s.

1.4.2 MSG47-ABD Gene PCR Amplification

MSG47-ABD gene PCR amplification uses Vazyme 2×Phanta Max Master Mix kit, and the specific reaction system is as follows:

| | | | | | | |
|---|---|---|---|---|---|---|
| Total volume | 15 μl | | | | | |
| Mix | 7.5 μl | | | | | |
| DNA | 1 μl | | | | | |
| Forward Primer | 0.5 μl | | | | | |
| Reverse Primer | 0.5 μl | | | | | |
| ddH₂0 | 5.5 μl | | | | | |

The reaction conditions are: MSG47-CRISP-WheatA: annealing temperature 60° C., extension time 1 min; MSG47-CRISP-WheatB: annealing temperature 60° C., extension time 1 min; MSG47-CRISP-WheatD: annealing temperature 62° C., extension time 2 min.

2. Experimental Results

Figure 5:
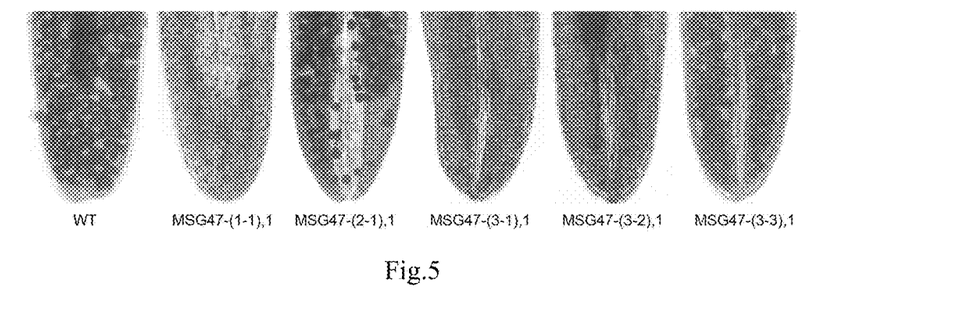
FIG. 5: phenotypic investigation of some progenies of gene editing

Using hexaploid common wheat Fielder as the recipient material, using *Agrobacterium*-mediated genetic transformation, a total of 6 independent T$_0$ generation transgenic plants were obtained. Bar gene detection (detection primer: P121/122) shows that 13 tillers of 5 strains MSG47-(1-1), MSG47-(2-1), MSG47-(3-1), MSG47-(3-2) are positive, and 2 tillers from 1 strain MSG 47-(5-1) are negative (Table 2), with a conversion rate of about 86.7%. Using MSG 47 specific amplification primers, MSG47-CRISP-WheatA-SF1/SR1, MSG47-CRISP-WheatB-SF2/SR2, MSG47-CRISP-WheatD-SF3/SR3, sequencing the tillers of all transgenic seedlings and analyzing the mutation of target genes, four editing situations are found in T$_0$ generation transgenic plants: homozygous editing (+/+), heterozygous editing (+/+'), one DNA chain editing another without editing (+/−) and no editing (−/−) (Table 2). The phenotype is further determined by Alexander staining, and three positive transgenic lines (MSG47-(1-1), MSG47-(3-1) and MSG47-(3-2)) are found to have homozygous or heterozygous editing on the target genes of the three subgenomes A, B and D, and all tillers showed abortion phenotype without pollen grain type (Table 2, FIG. 5). However, two positive transgenic lines (MSG47-(2-1) and MSG47-(3-3)) and one negative transgenic line (MSG 47-(5-1)) only have partial or no editing on the target genes of three subgenomes A, B and D, and all tillers are wild-type fertile phenotypes. By comparing the results of gene editing with the phenotypes, it is found that abortion phenotype occurs only when all three subgenomes A, B and D are edited, and fertile phenotype occurs only when one or two subgenomes or no subgenome editing occurs.

TABLE 2

Hvmsg47 Gene Edit Statistics

| Plant number | Tillers number | Bar gene detection result | Whether gene editing occurs in target gene | | | Phenotype |
|---|---|---|---|---|---|---|
| | | | MSG47-A | MSG47-B | MSG47-D | |
| MSG47-(1-1) | MSG47-(1-1), 1 | + | +/+' | +/+' | +/+ | S |
| | MSG47-(1-1), 2 | + | +/+' | +/+' | +/+ | S |
| | MSG47-(1-1), 3 | + | +/+' | +/+' | +/+ | S |
| | MSG47-(1-1), 4 | + | +/+' | +/+' | +/+ | S |
| | MSG47-(1-1), 5 | + | +/+' | +/+' | +/+ | S |
| MSG47-(2-1) | MSG47-(2-1), 1 | + | +/+ | −/− | −/− | F |
| | MSG47-(2-1), 2 | + | −/− | −/− | −/− | F |
| MSG47-(3-1) | MSG47-(3-1), 1 | + | +/+' | +/+' | +/+' | S |
| | MSG47-(3-1), 2 | + | +/+' | +/+' | +/+' | S |
| | MSG47-(3-1), 3 | + | +/+' | +/+' | +/+' | S |
| MSG47-(3-2) | MSG47-(3-2), 1 | + | +/+' | +/+' | +/+ | S |
| | MSG47-(3-2), 2 | + | +/+' | +/+' | +/+ | S |
| MSG47-(3-3) | MSG47-(3-3), 1 | + | +/− | +/+' | −/− | F |
| MSG47-(5-1) | MSG47-(5-1), 1 | − | −/− | −/− | −/− | F |
| | MSG47-(5-1), 2 | − | −/− | −/− | −/− | F |

Note:
"+" represents that the Bar gene test is positive, and "−" represents that the Bar gene test is negative; "+/+" represents homozygous editing of the wheat A, B or D subgenome; "+/+'" represents heterozygous editing of the wheat A, B or D subgenome; " +/−" represents that only one DNA chain of the wheat A, B or D subgenome is edited, and the other DNA chain is not edited; "−/−" represents that no gene editing occurs in the subgenome of wheat A, B or D; "F" stands for fertile and "S" stands for abortive.

Through the above functional verification experiments on transgenic plants, it is proved that the function of HvMsg47 gene is mainly to affect anther development and ultimately lead to the phenotype of male sterility.

The above are only preferred embodiments of the application, and are not used to limit the application, and for those skilled in the art, the application can be variously modified and varied. Any modification, equivalent substitution, improvement and the like made within the spirit and principle of the application shall be included in the protection scope of the application.

The invention claimed is:

1. A method of providing a male-sterility phenotype to a barley or wheat plant, comprising:
   genetically modifying the barley or wheat plant so as to obtain a genetically-modified plant that comprises a gene that provides the genetically-modified plant with the male-sterility phenotype when expressed; and
   propagating the genetically-modified plant to obtain progeny with the male-sterility phenotype,
   wherein the gene encodes an amino acid sequence, and the amino acid sequence has at least 99% sequence identity with SEQ ID NO: 3 and has at least one mutation with respect to SEQ ID NO: 3 that is selected from the group consisting of:
   a G74D mutation,
   a A202V mutation, and
   a V566E mutation.

2. The method of claim 1, wherein the barley or wheat plant is a barley plant.

3. The method of claim 1, wherein the barley or wheat plant is a wheat plant.

4. The method of claim 1, wherein the amino acid sequence has a G74D mutation with respect to SEQ ID NO: 3.

5. The method of claim 1, wherein the amino acid sequence has a A202V mutation with respect to SEQ ID NO: 3.

6. The method of claim 1, wherein the amino acid sequence has a V566E mutation with respect to SEQ ID NO: 3.

7. The method of claim 1, wherein the gene has a nucleotide sequence and the nucleotide sequence has at least 90% sequence identity with SEQ ID NO: 1.

8. The method of claim 1, wherein the gene has a coding nucleotide sequence and the coding nucleotide sequence has at least 90% sequence identity with SEQ ID NO: 2.

9. The method of claim 1, wherein the amino acid sequence consists of SEQ ID NO: 3 having at least one of the mutations.

\* \* \* \* \*

SEQUENCE LISTING

<160> NUMBER OF SEQ ID NOS: 29

<210> SEQ ID NO 1
<211> LENGTH: 2703

```
<212> TYPE: DNA
<213> ORGANISM: Barley(Hordeum vulgare L.)

<400> SEQUENCE: 1
atggggagct cgtgcgtgaa cctctcccgc gccgtcgcgg ccgcgaggcg cccgggcttc      60
ggcaccggcg ccggcggcca cgggagatgc gtggtcgcat tgtcgtcgtc gtcgtcgagg     120
aggcgcaccg ccgccgacgg tggcgtgtcg tgcggcatcg ccaacgggta cctgggcggc     180
ttgtctggtg ggtcgcggcc gccttccttg ccggtgcacg gcaagagttc cgggcccggt     240
tcggggcggg aggccggcga tcaggctgac gctgacgctg acgggctcgg gatccaggag     300
ttccttggcg gcaagaactt cctcatcacc ggcgggactg gcttcctagc aaaaggtact     360
atatcatcat cttcattttt ctctgtctcc tctccactcg attatctttg ctgttttcgt     420
gcttgatttc gctcgtgatt tcatttcagt tctgatcgag aaaatcctga ggaccaacac     480
tgacgtgggc aagatatacg tgctgatcaa ggccaaggac agcgagacgg cattgcagag     540
actgcaaaac gaggtatgat acgatgccta gaaaaggcca agttcccttt gccgctcatt     600
caaacgatga tgatattttc tcctgtgggc aggtggtgga cacggagctg ttcaagcgcc     660
tgcaggagat ccacgggaaa gactaccacg gattcatagc cacgaagctt gtccccgtag     720
ttggcgacgt ccgggaggcc aacatcggca ttgcccccga gctggccgat gagatcgcgg     780
agcgggtgga catcatcgtc aactccgccg ccaataccac tttcgacgag aggttcgttc     840
gtccgtcctt ctatagtccg tccacttggc ttctggtcta gtgtaaaaat actcgtctac     900
cacctagatt cagtcactcc ggtgcgacca aattcaagaa ttttacttgt gaatgttcaa     960
cctgcaggta cgatgttgcc atggacatca acaccgtggg gccgttccgg ataatgagct    1020
tcgcgcatcg gtttcgaagg ctcaagctct tcctgcaggt gtccacaggt gaggagggat    1080
catgccaact taatcttctt cttgtgaaag tgacatccat ggttttctta ttcgaggttt    1140
ccaacggttg tgtcgcatga catccatgca tgatctctgc agcgtatgtg aacgggcaga    1200
ggcagggtgt cgtgctggag aaaccgtttc ggttgggtga caccatagga aaagggtcag    1260
ctggatcctc ggattcttcg gagcagcaca agaacgccgt gctcgacatc gaggcggaga    1320
tcaagctggc cttcgactcg agaagccgcg ccgatgatga cccggcttct ttctctcagg    1380
agatgaagga tttagggcta gagaggtacg caagatgtgc atttcttacc atgacctcct    1440
cggtctcagc ctgaaggtgc aacattcatt tgatttgctg aacgtgttgg ttgctcttat    1500
atatatatat atagagcgaa gctccatggg tggcaggaca cgtacgtgtt caccaaggcc    1560
atgggggaga tggtgatcaa cagcatgcga ggggagatcc ccgtggtgac catcaggccc    1620
agcgtcatcg agagcacctg gagagacccc ttcccgggct ggatggaagg caacaggtac    1680
gtacgtgcgt gcgtgcgtgc agattgtgct ataatcctgc agagttcacc aacatcctgt    1740
gctgatttct gtgggcgaat cggtttggtc cgtcaggatg atggaccctg tcgtcctcta    1800
ctacggcaaa ggccagctga gcgggttcct cgccgacccg gccggcgttc tagacgtggt    1860
aatcaatcgg tcacgcacgc attccctaac caaatgtacc ccgtagtagc tagtgagacc    1920
atggaagatg atcttgcagg cgctaatggc tttctcgttg tgtcactggg caaggttccg    1980
gcggacatgg tggtgaacgc gacgctggcg gcgatggcga agcacgggcg ggcggcggag    2040
gggggaatgc acgtgtacca cgtggcgtcg tcgacggtga cccgctggt gttcggcgac    2100
ctgagccggt tcctgttcca gcacttcacg agcagcccct acagcgacgc ggcggggcag    2160
cccatcgccg tgccgcccat gcgcctcttc gacaccatgg agcagttcgc cagctacgtc    2220
```

| | |
|---|---:|
| gagacggacg cgctgctccg gagcgccagg gccggcgccc ccgccggcga gcgcctctcg | 2280 |
| cagcgcctcc aggagctctg cgccaagtcc gtcgagcaga ccatccacct cggcagcatc | 2340 |
| taccagccgt acaccttcta caccggcagg tgatccctcc atctctctct ctttctcgcc | 2400 |
| catggcgcta ccgtttgtgc acgcatatgt tttgtctgct cacgccgcta ccatcgacat | 2460 |
| gggcgcaggt tcgacaactg caacacggaa gggctcatgg cggagatgtc ggcgcaggag | 2520 |
| aaggcagggt tccacttcga cgtgcggagc atcgactgga cggactacat caccaacgtc | 2580 |
| cacatcccgg ggctcaggaa gcacgtcatg aaagggaggg gcatcgccgc cacctcctcc | 2640 |
| tcaccgtcgg catccccgtc cacgatggag gagctcgccg cagccagcgc ctccgctgtg | 2700 |
| tga | 2703 |

<210> SEQ ID NO 2
<211> LENGTH: 1857
<212> TYPE: DNA
<213> ORGANISM: Barley(Hordeum vulgare L.)

<400> SEQUENCE: 2

| | |
|---|---:|
| atggggagct cgtgcgtgaa cctctcccgc gccgtcgcgg ccgcgaggcg cccgggcttc | 60 |
| ggcaccggcg ccggcggcca cgggagatgc gtggtcgcat tgtcgtcgtc gtcgtcgagg | 120 |
| aggcgcaccg ccgccgacgg tggcgtgtcg tgcggcatcg ccaacgggta cctgggcggc | 180 |
| ttgtctggtg ggtcgcggcc gccttccttg ccggtgcacg gcaagagttc cgggcccggt | 240 |
| tcggggcggg aggccggcga tcaggctgac gctgacgctg acgggctcgg gatccaggag | 300 |
| ttccttggcg gcaagaactt cctcatcacc ggcgggactg gcttcctagc aaaagttctg | 360 |
| atcgagaaaa tcctgaggac caacactgac gtgggcaaga tatacgtgct gatcaaggcc | 420 |
| aaggacagcg agacggcatt gcagagactg caaaacgagg tggtggacac ggagctgttc | 480 |
| aagcgcctgc aggagatcca cgggaaagac taccacggat tcatagccac gaagcttgtc | 540 |
| cccgtagttg gcgacgtccg ggaggccaac atcggcattg ccccgagct ggccgatgag | 600 |
| atcgcggagc gggtggacat catcgtcaac tccgccgcca ataccacttt cgacgagagg | 660 |
| tacgatgttg ccatggacat caacaccgtg gggccgttcc ggataatgag cttcgcgcat | 720 |
| cggtttcgaa ggctcaagct cttcctgcag gtgtccacag cgtatgtgaa cgggcagagg | 780 |
| cagggtgtcg tgctggagaa accgtttcgg ttgggtgaca ccataggaaa agggtcagct | 840 |
| ggatcctcgg attcttcgga gcagcacaag aacgccgtgc tcgacatcga ggcggagatc | 900 |
| aagctggcct tcgactcgag aagccgcgcc gatgatgacc cggcttcttt ctctcaggag | 960 |
| atgaaggatt tagggctaga gagagcgaag ctccatgggt ggcaggacac gtacgtgttc | 1020 |
| accaaggcca tggggagat ggtgatcaac agcatgcgag gggagatccc cgtggtgacc | 1080 |
| atcaggccca gcgtcatcga gagcacctgg agagaccct tcccgggctg gatggaaggc | 1140 |
| aacaggatga tggaccctgt cgtcctctac tacggcaaag gccagctgag cgggttcctc | 1200 |
| gccgacccgg ccggcgttct agacgtggtt ccggcggaca tggtggtgaa cgcgacgctg | 1260 |
| gcggcgatgg cgaagcacgg gcgggcggcg gagggggaa tgcacgtgta ccacgtggcg | 1320 |
| tcgtcgacgg tgaacccgct ggtgttcggc gacctgagcc ggttcctgtt ccagcacttc | 1380 |
| acgagcagcc cctacagcga cgcggcgggg cagcccatcg ccgtgccgcc catgcgcctc | 1440 |
| ttcgacacca tggagcagtt cgccagctac gtcgagacgg acgcgctgct ccggagcgcc | 1500 |
| agggccggcg ccccgccgg cgagcgcctc tcgcagcgcc tccaggagct ctgcgccaag | 1560 |
| tccgtcgagc agaccatcca cctcggcagc atctaccagc cgtacacctt ctacaccggc | 1620 |

-continued

```
aggttcgaca actgcaacac ggaagggctc atggcggaga tgtcggcgca ggagaaggca   1680
gggttccact tcgacgtgcg gagcatcgac tggacggact acatcaccaa cgtccacatc   1740
ccggggctca ggaagcacgt catgaaaggg agggcatcg ccgccacctc ctcctcaccg    1800
tcggcatccc cgtccacgat ggaggagctc gccgcagcca gcgcctccgc tgtgtga      1857
```

<210> SEQ ID NO 3
<211> LENGTH: 618
<212> TYPE: PRT
<213> ORGANISM: Barley(Hordeum vulgare L.)

<400> SEQUENCE: 3

```
Met Gly Ser Ser Cys Val Asn Leu Ser Arg Ala Val Ala Ala Arg
1               5                   10                  15

Arg Pro Gly Phe Gly Thr Gly Ala Gly His Gly Arg Cys Val Val
                20                  25                  30

Ala Leu Ser Ser Ser Ser Arg Arg Thr Ala Ala Asp Gly Gly
            35                  40                  45

Val Ser Cys Gly Ile Ala Asn Gly Tyr Leu Gly Gly Leu Ser Gly Gly
        50                  55                  60

Ser Arg Pro Pro Ser Leu Pro Val His Gly Lys Ser Ser Gly Pro Gly
65                  70                  75                  80

Ser Gly Arg Glu Ala Gly Asp Gln Ala Asp Ala Asp Gly Leu
                85                  90                  95

Gly Ile Gln Glu Phe Leu Gly Gly Lys Asn Phe Leu Ile Thr Gly Gly
                100                 105                 110

Thr Gly Phe Leu Ala Lys Val Leu Ile Glu Lys Ile Leu Arg Thr Asn
            115                 120                 125

Thr Asp Val Gly Lys Ile Tyr Val Leu Ile Lys Ala Lys Asp Ser Glu
130                 135                 140

Thr Ala Leu Gln Arg Leu Gln Asn Glu Val Val Asp Thr Glu Leu Phe
145                 150                 155                 160

Lys Arg Leu Gln Glu Ile His Gly Lys Asp Tyr His Gly Phe Ile Ala
                165                 170                 175

Thr Lys Leu Val Pro Val Val Gly Asp Val Arg Glu Ala Asn Ile Gly
            180                 185                 190

Ile Ala Pro Glu Leu Ala Asp Glu Ile Ala Glu Arg Val Asp Ile Ile
        195                 200                 205

Val Asn Ser Ala Ala Asn Thr Thr Phe Asp Glu Arg Tyr Asp Val Ala
    210                 215                 220

Met Asp Ile Asn Thr Val Gly Pro Phe Arg Ile Met Ser Phe Ala His
225                 230                 235                 240

Arg Phe Arg Arg Leu Lys Leu Phe Leu Gln Val Ser Thr Ala Tyr Val
                245                 250                 255

Asn Gly Gln Arg Gln Gly Val Val Leu Glu Lys Pro Phe Arg Leu Gly
            260                 265                 270

Asp Thr Ile Gly Lys Gly Ser Ala Gly Ser Ser Asp Ser Ser Glu Gln
        275                 280                 285

His Lys Asn Ala Val Leu Asp Ile Glu Ala Glu Ile Lys Leu Ala Phe
    290                 295                 300

Asp Ser Arg Ser Arg Ala Asp Asp Pro Ala Ser Phe Ser Gln Glu
305                 310                 315                 320

Met Lys Asp Leu Gly Leu Glu Arg Ala Lys Leu His Gly Trp Gln Asp
                325                 330                 335
```

```
Thr Tyr Val Phe Thr Lys Ala Met Gly Glu Met Val Ile Asn Ser Met
                340                 345                 350
Arg Gly Glu Ile Pro Val Val Thr Ile Arg Pro Ser Val Ile Glu Ser
            355                 360                 365
Thr Trp Arg Asp Pro Phe Pro Gly Trp Met Gly Asn Arg Met Met
370                 375                 380
Asp Pro Val Val Leu Tyr Tyr Gly Lys Gly Gln Leu Ser Gly Phe Leu
385                 390                 395                 400
Ala Asp Pro Ala Gly Val Leu Asp Val Pro Ala Asp Met Val Val
                405                 410                 415
Asn Ala Thr Leu Ala Ala Met Ala Lys His Gly Arg Ala Ala Glu Gly
                420                 425                 430
Gly Met His Val Tyr His Val Ala Ser Ser Thr Val Asn Pro Leu Val
                435                 440                 445
Phe Gly Asp Leu Ser Arg Phe Leu Phe Gln His Phe Thr Ser Ser Pro
    450                 455                 460
Tyr Ser Asp Ala Ala Gly Gln Pro Ile Ala Val Pro Pro Met Arg Leu
465                 470                 475                 480
Phe Asp Thr Met Glu Gln Phe Ala Ser Tyr Val Glu Thr Asp Ala Leu
                485                 490                 495
Leu Arg Ser Ala Arg Ala Gly Ala Pro Ala Gly Glu Arg Leu Ser Gln
                500                 505                 510
Arg Leu Gln Glu Leu Cys Ala Lys Ser Val Glu Gln Thr Ile His Leu
                515                 520                 525
Gly Ser Ile Tyr Gln Pro Tyr Thr Phe Tyr Thr Gly Arg Phe Asp Asn
                530                 535                 540
Cys Asn Thr Glu Gly Leu Met Ala Glu Met Ser Ala Gln Glu Lys Ala
545                 550                 555                 560
Gly Phe His Phe Asp Val Arg Ser Ile Asp Trp Thr Asp Tyr Ile Thr
                565                 570                 575
Asn Val His Ile Pro Gly Leu Arg Lys His Val Met Lys Gly Arg Gly
                580                 585                 590
Ile Ala Ala Thr Ser Ser Ser Pro Ser Ala Ser Pro Ser Thr Met Glu
                595                 600                 605
Glu Leu Ala Ala Ala Ser Ala Ser Ala Val
    610                 615
```

<210> SEQ ID NO 4
<211> LENGTH: 23
<212> TYPE: DNA
<213> ORGANISM: Artificial sequence
<220> FEATURE:
<223> OTHER INFORMATION: Primer

<400> SEQUENCE: 4
cttcaataca tttccagacc ggc                                          23

<210> SEQ ID NO 5
<211> LENGTH: 25
<212> TYPE: DNA
<213> ORGANISM: Artificial sequence
<220> FEATURE:
<223> OTHER INFORMATION: Primer

<400> SEQUENCE: 5
acttacaata ccttgctgaa tgggc                                        25

```
<210> SEQ ID NO 6
<211> LENGTH: 23
<212> TYPE: DNA
<213> ORGANISM: Artificial sequence
<220> FEATURE:
<223> OTHER INFORMATION: Primer

<400> SEQUENCE: 6
ctcatttcga gctgagagag agc                                              23

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
cctatcgggc atttgttcac cg                                               22

<210> SEQ ID NO 8
<211> LENGTH: 21
<212> TYPE: DNA
<213> ORGANISM: Artificial sequence
<220> FEATURE:
<223> OTHER INFORMATION: Primer

<400> SEQUENCE: 8
ctcttcgaca ccatggagca g                                                21

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
caaaacatat gcgtgcacaa acgg                                             24

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
aaaagtcata ctgccacggt ccg                                              23

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
agtagggaaa tcttgctccc ctc                                              23

<210> SEQ ID NO 12
<211> LENGTH: 25
<212> TYPE: DNA
<213> ORGANISM: Artificial sequence
<220> FEATURE:
<223> OTHER INFORMATION: Primer
```

<400> SEQUENCE: 12
ttcccctcct tcctgtatcg gcccg							25

<210> SEQ ID NO 13
<211> LENGTH: 22
<212> TYPE: DNA
<213> ORGANISM: Artificial sequence
<220> FEATURE:
<223> OTHER INFORMATION: Primer

<400> SEQUENCE: 13
atccccgtgc cgggcgcttt ga							22

<210> SEQ ID NO 14
<211> LENGTH: 24
<212> TYPE: DNA
<213> ORGANISM: Artificial sequence
<220> FEATURE:
<223> OTHER INFORMATION: Primer

<400> SEQUENCE: 14
tgttcagagg gagtaaacta tcga							24

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
catggatgtc atgcgacaca ac							22

<210> SEQ ID NO 16
<211> LENGTH: 23
<212> TYPE: DNA
<213> ORGANISM: Artificial sequence
<220> FEATURE:
<223> OTHER INFORMATION: Primer

<400> SEQUENCE: 16
taccacctag attcagtcac tcc							23

<210> SEQ ID NO 17
<211> LENGTH: 24
<212> TYPE: DNA
<213> ORGANISM: Artificial sequence
<220> FEATURE:
<223> OTHER INFORMATION: Primer

<400> SEQUENCE: 17
gaacaaacct ggtacaatga catc							24

<210> SEQ ID NO 18
<211> LENGTH: 23
<212> TYPE: DNA
<213> ORGANISM: Wheat(Triticum aestivum L.)

<400> SEQUENCE: 18
ccttgccggt gcacggcaag agc							23

<210> SEQ ID NO 19
<211> LENGTH: 23
<212> TYPE: DNA

<213> ORGANISM: Wheat(Triticum aestivum L.)

<400> SEQUENCE: 19
ccaccttcga cgagaggttc gtc                           23

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
aagcacggtc aacttccgta                               20

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
gaagtccagc tgccagaaac                               20

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
ccgatcagct ccaccatcac                               20

<210> SEQ ID NO 23
<211> LENGTH: 22
<212> TYPE: DNA
<213> ORGANISM: Artificial sequence
<220> FEATURE:
<223> OTHER INFORMATION: Primer

<400> SEQUENCE: 23
atcttggagc agtgcaaaca gc                            22

<210> SEQ ID NO 24
<211> LENGTH: 19
<212> TYPE: DNA
<213> ORGANISM: Artificial sequence
<220> FEATURE:
<223> OTHER INFORMATION: Primer

<400> SEQUENCE: 24
ctagcccgta cctgacgac                                19

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
atggcatgag cctgacctgt g                             21

```
<210> SEQ ID NO 26
<211> LENGTH: 21
<212> TYPE: DNA
<213> ORGANISM: Artificial sequence
<220> FEATURE:
<223> OTHER INFORMATION: Primer

<400> SEQUENCE: 26
ctttccgtgt tcttcccaca c                                              21

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
agaccgagac caagaggagg                                                20

<210> SEQ ID NO 28
<211> LENGTH: 11
<212> TYPE: PRT
<213> ORGANISM: Barley (Hordeum vulgare L.)

<400> SEQUENCE: 28

Ser Ile Tyr Gln Pro Tyr Thr Phe Tyr Thr Gly
1               5                   10

<210> SEQ ID NO 29
<211> LENGTH: 618
<212> TYPE: PRT
<213> ORGANISM: Artificial Sequence
<220> FEATURE:
<223> OTHER INFORMATION: variant of protein encoded by HvMSG47
<220> FEATURE:
<221> NAME/KEY: VARIANT
<222> LOCATION: (1)..(618)
<223> OTHER INFORMATION: 74X is Gly or Asp; 202X is Ala or Val; 566 is
      Val or Glu; wherein at least one of the amino acid residues at
      these positions differs from the amino acid at the corresponding
      position in SEQ ID NO: 3

<400> SEQUENCE: 29

Met Gly Ser Ser Cys Val Asn Leu Ser Arg Ala Val Ala Ala Ala Arg
1               5                   10                  15

Arg Pro Gly Phe Gly Thr Gly Ala Gly Gly His Gly Arg Cys Val Val
                20                  25                  30

Ala Leu Ser Ser Ser Ser Arg Arg Arg Thr Ala Ala Asp Gly Gly
        35                  40                  45

Val Ser Cys Gly Ile Ala Asn Gly Tyr Leu Gly Gly Leu Ser Gly Gly
    50                  55                  60

Ser Arg Pro Pro Ser Leu Pro Val His Xaa Lys Ser Ser Gly Pro Gly
65                  70                  75                  80

Ser Gly Arg Glu Ala Gly Asp Gln Ala Asp Ala Asp Ala Asp Gly Leu
                85                  90                  95

Gly Ile Gln Glu Phe Leu Gly Gly Lys Asn Phe Leu Ile Thr Gly Gly
            100                 105                 110

Thr Gly Phe Leu Ala Lys Val Leu Ile Glu Lys Ile Leu Arg Thr Asn
        115                 120                 125

Thr Asp Val Gly Lys Ile Tyr Val Leu Ile Lys Ala Lys Asp Ser Glu
    130                 135                 140

Thr Ala Leu Gln Arg Leu Gln Asn Glu Val Val Asp Thr Glu Leu Phe
```

```
            145                 150                 155                 160
        Lys Arg Leu Gln Glu Ile His Gly Lys Asp Tyr His Gly Phe Ile Ala
                        165                 170                 175
        Thr Lys Leu Val Pro Val Val Gly Asp Val Arg Glu Ala Asn Ile Gly
                        180                 185                 190
        Ile Ala Pro Glu Leu Ala Asp Glu Ile Xaa Glu Arg Val Asp Ile Ile
                        195                 200                 205
        Val Asn Ser Ala Ala Asn Thr Thr Phe Asp Gly Arg Tyr Asp Val Ala
            210                 215                 220
        Met Asp Ile Asn Thr Val Gly Pro Phe Arg Ile Met Ser Phe Ala His
        225                 230                 235                 240
        Arg Phe Arg Arg Leu Lys Leu Phe Leu Gln Val Ser Thr Ala Tyr Val
                        245                 250                 255
        Asn Gly Gln Arg Gln Gly Val Val Leu Glu Lys Pro Phe Arg Leu Gly
                        260                 265                 270
        Asp Thr Ile Gly Lys Gly Ser Ala Gly Ser Ser Asp Ser Ser Glu Gln
                        275                 280                 285
        His Lys Asn Ala Val Leu Asp Ile Glu Ala Glu Ile Lys Leu Ala Phe
            290                 295                 300
        Asp Ser Arg Ser Arg Ala Asp Asp Pro Ala Ser Phe Ser Gln Glu
        305                 310                 315                 320
        Met Lys Asp Leu Gly Leu Glu Arg Ala Lys Leu His Gly Trp Gln Asp
                        325                 330                 335
        Thr Tyr Val Phe Thr Lys Ala Met Gly Glu Met Val Ile Asn Ser Met
                        340                 345                 350
        Arg Gly Glu Ile Pro Val Val Thr Ile Arg Pro Ser Val Ile Glu Ser
                        355                 360                 365
        Thr Trp Arg Asp Pro Phe Pro Gly Trp Met Glu Gly Asn Arg Met Met
                        370                 375                 380
        Asp Pro Val Val Leu Tyr Tyr Gly Lys Gly Gln Leu Ser Gly Phe Leu
        385                 390                 395                 400
        Ala Asp Pro Ala Gly Val Leu Asp Val Val Pro Ala Asp Met Val Val
                        405                 410                 415
        Asn Ala Thr Leu Ala Ala Met Ala Lys His Gly Arg Ala Ala Glu Gly
                        420                 425                 430
        Gly Met His Val Tyr His Val Ala Ser Ser Thr Val Asn Pro Leu Val
                        435                 440                 445
        Phe Gly Asp Leu Ser Arg Phe Leu Phe Gln His Phe Thr Ser Ser Pro
            450                 455                 460
        Tyr Ser Asp Ala Ala Gly Gln Pro Ile Ala Val Pro Pro Met Arg Leu
        465                 470                 475                 480
        Phe Asp Thr Met Glu Gln Phe Ala Ser Tyr Val Glu Thr Asp Ala Leu
                        485                 490                 495
        Leu Arg Ser Ala Arg Ala Gly Ala Pro Ala Gly Glu Arg Leu Ser Gln
                        500                 505                 510
        Arg Leu Gln Glu Leu Cys Ala Lys Ser Val Glu Gln Thr Ile His Leu
                        515                 520                 525
        Gly Ser Ile Tyr Gln Pro Tyr Thr Phe Tyr Thr Gly Arg Phe Asp Asn
            530                 535                 540
        Cys Asn Thr Glu Gly Leu Met Ala Glu Met Ser Ala Gln Glu Lys Ala
        545                 550                 555                 560
        Gly Phe His Phe Asp Xaa Arg Ser Ile Asp Trp Thr Asp Tyr Ile Thr
                        565                 570                 575
```

```
Asn Val His Ile Pro Gly Leu Arg Lys His Val Met Lys Gly Arg Gly
            580                 585                 590

Ile Ala Ala Thr Ser Ser Ser Pro Ser Ala Ser Pro Ser Thr Met Glu
            595                 600                 605

Glu Leu Ala Ala Ala Ser Ala Ser Ala Val
            610                 615
```